United States Patent [19]
Marsh et al.

[11] 4,250,875
[45] Feb. 17, 1981

[54] CANINE EAR STRENGTHENING AND TRAINING DEVICE

[76] Inventors: Thomas E. Marsh; Pamela S. Marsh, both of R.R. 1, Box 251, Parker City, Ind. 47368

[21] Appl. No.: 9,230

[22] Filed: Feb. 2, 1979

[51] Int. Cl.$^3$ ........................ A61F 13/00; A01K 29/00

[52] U.S. Cl. ........................................ 128/82; 128/133; 119/96

[58] Field of Search .................... 128/68, 76 K, 76 D, 128/82, 95, 97, 89 R, 132 R, 133, 134, 135, 346, 330, 151, 152; 119/96; 40/301, 303, 302

[56] References Cited

U.S. PATENT DOCUMENTS

| | | | |
|---|---|---|---|
| 714,850 | 12/1902 | Zimmermann | 128/346 |
| 2,442,176 | 5/1948 | Orr et al. | 128/133 |
| 3,257,990 | 6/1966 | Robertson et al. | 128/346 |
| 3,301,253 | 1/1967 | Glorig | 128/97 |
| 3,970,080 | 7/1976 | White | 119/96 |
| 4,003,376 | 1/1977 | McKay et al. | 128/69 |
| 4,059,106 | 11/1977 | Shannon | 128/133 |
| 4,148,279 | 4/1979 | Hoytt | 119/96 |
| 4,161,946 | 7/1979 | Zuesse | 128/75 |

*Primary Examiner*—Robert W. Michell
*Assistant Examiner*—Arthur S. Rose
*Attorney, Agent, or Firm*—Cross, Marshall, Schuck & Deweese

[57] ABSTRACT

A device for strengthening and training the auricular muscles of dogs to hold ears erect following cosmetic surgery, comprising a transverse member affixed to the upper ends of two columnar shafts and extending between them perpendicularly. The shafts are inserted into the ear canals of the animal activating a reflexive response of the auricular muscles causing the ears to remain in an erect position. The device is held in place by the application of adhesive tape or other securing means about the shaft and the ear.

1 Claim, 3 Drawing Figures

CANINE EAR STRENGTHENING AND TRAINING DEVICE

BACKGROUND OF THE INVENTION

The present invention relates to an improved device for strengthening the auricular muscles of dogs, particularly in situations where a dog's ears have undergone cosmetic surgery.

In certain breeds of dogs it is thought desirable to surgically remove a portion of the outer ear and subsequently train the ear to stand erect independent of artificial support. For example, some types of dogs are trained and displayed at shows and exhibitions in competition. It is considered desirable by those persons who train such dogs that the ears of these animals be cropped and subsequently trained to stand erect. Such a result is obtained by strengthening and training the auricular muscles of the animal so that they are capable of holding the weight of the ear in an erect position. It has been found that this process should take place while the dog is very young, in that it becomes increasingly difficult to train the dog and condition the proper muscles as the dog becomes older.

At the present time there are a great many methods being employed by animal trainers, breeders, veterinarians and others to achieve these ends. The majority of the devices and methods are cumbersome and inefficient, and all are less effective and more difficult to apply in practice than the present invention. A common method of training auricular muscles currently in use consists of packing the ears with a filler material such as cotton and then applying a large number of strips of adhesive tape to the ear. Difficult and time consuming to apply, the resulting construct is also quite irritating to the animal. Another disadvantage of this method lies in the ease in which the dog may remove it by clawing at the assembly or rubbing its head against other objects. Additionally, if the tape is not applied correctly, or if some of the tape is torn off by the animal itself, the process may be ineffective to achieve the desired results.

Another common practice consists of placing an inverted paper cup upon the crown of the animal's head, and wrapping gauze around both ears and the cup, followed with a layer of adhesive tape. This method also entails the use of a fragile construct, the cup assembly being easily dislodged. As is the case with many other methods, it is extremely difficult to properly apply the materials so as to correctly train the ears. Other methods existing at present involve the use of wire or metal frames or devices of one sort or another. In addition to being cumbersome, these devices are difficult to keep properly positioned, resulting in ineffective training of the auricular muscles. Moreover, dogs wearing the devices may be subject to injury or disfigurement as a result of impact upon the device, either as a result of contact with other animals or of the efforts of the subject dog itself in trying to remove it. Such a result is even more likely when the device is heavy in weight, as is the case with many of the devices currently in use.

Yet another method is taught by U.S. Pat. No. 3,970,080, and consists of the application of a soft, pliable supporting body to the interior surface of the ear. The supporting body conforms exactly in size and shape to the interior of the ear of a particular animal and must therefore be custom made with the use of a mold. Accordingly, the device may not be used on more than one dog, and will be rendered obsolete should the animal outgrow it before the need for its use is ended. In addition to the disadvantages inherent in the task of creating a mold of a dog's ear, the method of securing the body to the ear as taught by the patent itself is difficult and tedious. Suturing the body to the ear is suggested as one such method, while another involves the application of layers of adhesive material. Either one necessarily requires that the subject animal be sedated for long periods of time.

SUMMARY OF THE INVENTION

The present invention was developed in an effort to circumvent the disadvantages existing in the methods and devices of the prior art. A simple, inexpensive strengthening and training device is created from a lightweight yet fairly rigid material such as strong plastic. Production of such strengtheners on a large scale can be easily accomplished by using molds of various shapes and sizes.

Two columnar shafts extending from the transverse member are inserted into the dog's ear canals causing the animal's auricular muscles to tighten in a reflexive response to the presence of the shafts in the ears. The tension exerted by the muscles over the period of time a device is in place has the effect of strengthening the muscles to a point where they are able to hold the ear erect without the stimulus of the device. Simultaneously with the strengthening of the ear, the reflex action caused by the continuous presence of the device trains the ear to remain erect once the device is removed.

The device is very quickly and easily applied by inserting the shafts into the ear canals of the animal and applying a relatively small amount of adhesive tape around the ear and the shaft together. Light in weight, the device causes little irritation to the animal, yet is securely positioned so as to retard displacement. A harness or bridle can be attached to the device and secured around the animal's head to achieve even more stability. The device can be reused on other animals of similar ear structure, although its inexpensive cost makes disposal after use economically feasible as well.

It is contemplated that a set of devices of varying shapes and dimensions will be employed by a user so as to adapt to any size animal. One embodiment of the invention features a construction with the two shafts and the transverse member being separate and independent pieces fitted with means enabling the shafts to be attached to the transverse member. By positioning the individual pieces as desired, the length of the transverse member between the shafts may be varied to accommodate animals with differing skull sizes. By proper vertical placement of the transverse member with respect to the shafts, the device can obtain additional stability by resting snugly on the animal's head while at the same time not making the animal uncomfortable.

Accordingly, it is an object of the invention to provide an improved device which will effectively strengthen and train an animal's auricular muscles so that following use of the device the animal's ears will remain erect.

Another object is to provide such a device that is inexpensive to produce, and that can economically be reused or disposed of as desired by the user.

Another object is to provide a device as aforesaid that is simple to use and can be applied quickly and easily, while remaining fixed in position and retarding displacement.

An additional object of the invention is to provide such a device that can be constructed in a variety of shapes and sizes to accommodate different animals, or can be constructed of individualized pieces which can be adjustably assembled for use on different animals.

Other objects and features of the invention are to be found in the following description and claims.

DESCRIPTION OF THE DRAWINGS

Drawings accompany the disclosure and the various views thereof may be briefly described as.

DESCRIPTION OF THE PREFERRED EMBODIMENT

Figure 1:
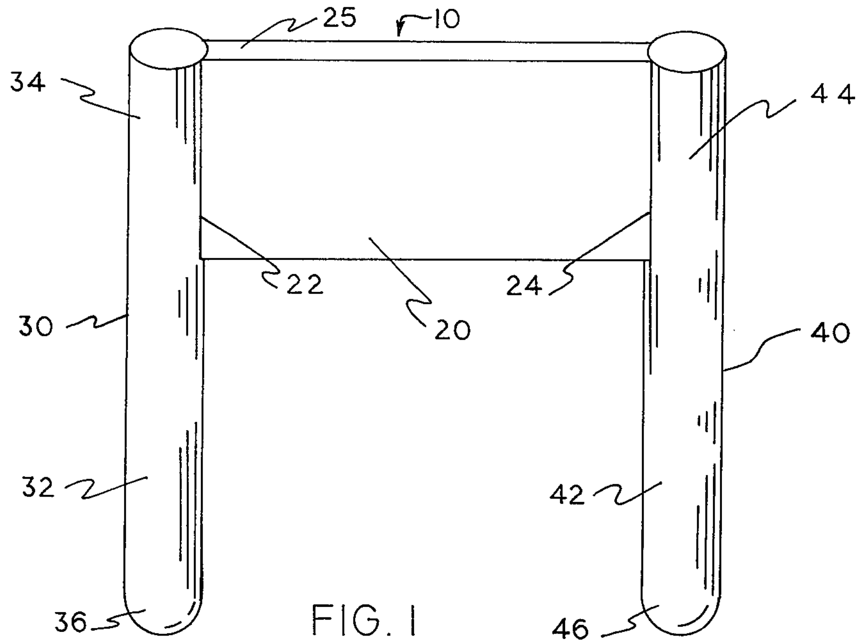
FIG. 1, a frontal view of the device taken at a slight elevation.

Referring now to the drawings, there is shown in FIG. 1 a canine ear strengthening and training device 10 which in the embodiment depicted is of unitary construction from a rigid yet lightweight material such as strong plastic. The device has three principal elements, namely: a transverse member 20, and two columnar shafts 30 and 40.

The lower portions 32 and 42 of the shafts 30 and 40 are shaped in any manner which will permit their entry into the left and right ear canals respectively of the animal whose ear muscles are to be strengthened and trained. The device shown in FIG. 1 features shafts 30 and 40 which are cylindrical in shape both in the lower portions 32 and 42 and in the upper portions 34 and 44. The lower ends of both shafts should be smooth surfaced in order to prevent any injury to the animal's internal ear which possibly might result if the tips possess any sharp corners or edges. In the preferred embodiment, the tips 36 and 46 of the lower ends of the two shafts are hemispherical in shape for this reason. Although the shafts featured in the drawing are in the shape found by experience to be most effective, a right circular cylinder, other tubular conformations, such as a cylindroid, may be employed.

The transverse member 20 is joined at right angles along its lateral ends 22 and 24 to the upper portions 34 and 44 of the two shafts respectively. In the preferred embodiment, the transverse member 20 is flat and rectangular, with a thickness roughly equivalent to the radius of the shaft. The transverse member can be of greater or lesser thickness than as shown and may even be hollow depending upon the rigidity and strength of the material being used. The transverse member can even be of varying thickness should this be necessitated by the particularities of the size and shape of the subject animal's head or of the material being used. The transverse member may be of any shape or configuration so long as it is capable of rigidly supporting the shafts so as to prevent any angular or vertical movement or displacement. The transverse member should be of a length corresponding to the width of the animal's head, so that the shafts 30 and 40 attached thereto are spaced symmetrically apart and can be inserted into the animal's ear canals.

Figure 2:
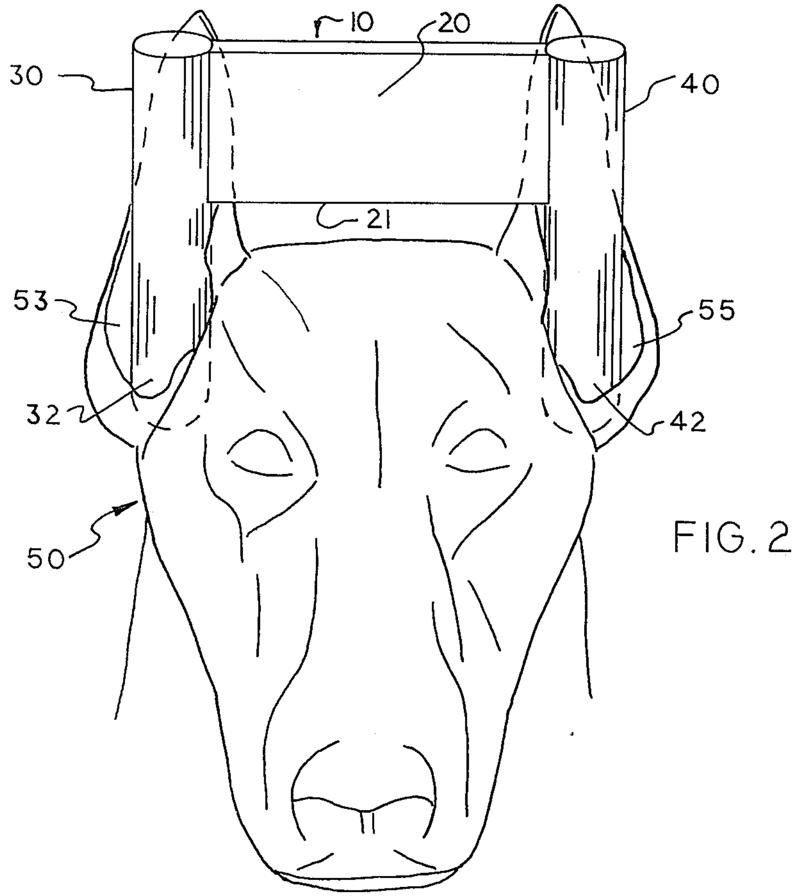
FIG. 2, a pictorial frontal view of the device positioned on the head of a dog.

Disclosed in FIG. 2 is the canine ear strengthening and training device 10 set in place upon the head of a dog 50. The lower portions 32 and 42 of the shafts 30 and 40 have been inserted into the ear canals 53 and 55 of the animal. In practice, the device should be constructed so that when the lower tips of the shafts are resting as far into the canal as desired, the underside 21 of the transverse member 20 loosely rests upon the head of the animal. This result can easily be achieved by predetermining the depth of the ear canal of the animal being worked with, and then manufacturing the shaft in a length calculated to achieve this purpose.

Figure 3:
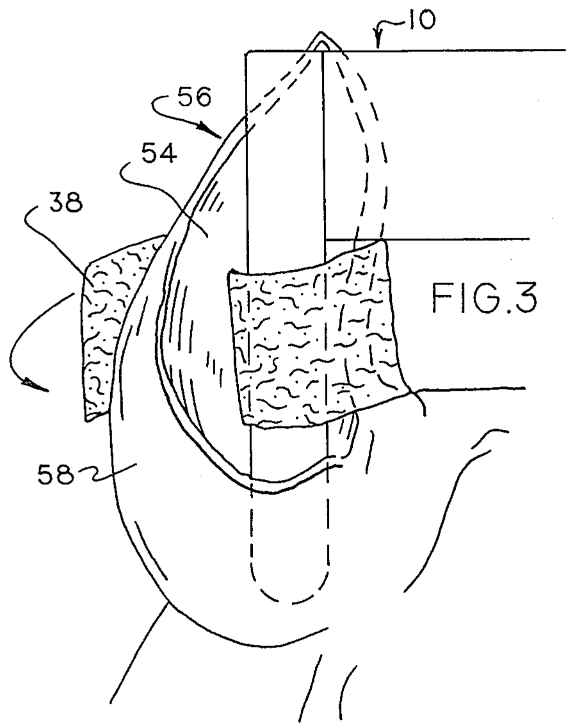
FIG. 3, a partial view of the device positioned and secured on the head of a dog.

As shown in FIG. 3 once the device 10 has been inserted into place it is then secured to the helix 54 of the dog's ear 56 so as to anchor the device to the animal's head. As the drawing illustrates, the device 10 may be secured easily and efficiently by wrapping a piece of adhesive tape 38 around the earlobe 58 and the shaft in each ear. It is envisioned that any conventional means may be used to secure the device to the animal's ear where practical, however adhesive tape appears to accomplish all desired purposes with a minimum investment of time and effort. Moreover, if carefully applied on both ears the tape projects outward from the surface of the ear only slightly, rendering it difficult for the subject animal or another to dislodge the device by clawing or scratching at the securing means. At the same time the device is fastened to the ear securely enough to prevent disengagement. To obtain still more stability the device may be incorporated into a bridle or harness assembly fastened about the dog's head and neck.

The device may be constructed in a variety of sizes, varying the length, width and thickness of the shafts and transverse member to accommodate different sizes and breeds of dogs. A veterinarian or other person interested in strengthening the ear muscles of animals may desire to keep on hand a set of assorted sizes and shapes of the device in order to service a large number and variety of animals. Depending upon the economics of construction, a used device may be disposed of and replaced with another, or cleaned and reused on another dog of similar stature.

It is contemplated that the device will be constructed in an embodiment where the transverse member and both shafts are individual pieces, as opposed to the unitary construction of FIG. 1. Each of the shafts as well as the transverse member possess some conventional fastening means which enable the user of the device to adjust the spacing of the shafts from one another in terms of position upon the transverse member as is presently done in other devices. However, it is possible in this manner to also adjust the vertical position of the transverse member with respect to the shafts. In this fashion one device may be adjusted to fit a large number of animals with heads of different sizes and ear canals of varying depths.

It will thus be seen that there is disclosed an animal ear strengthening device that is easily and efficiently constructed and applied which is also capable of modification for adaptation to a wide variety of dogs.

We claim:

1. A canine ear strengthening and training device to be secured upon the head of a dog which comprises:

two columnar shafts each having an upper and a lower end, the lower end of said shafts being shaped for insertion into the ear canals of a dog, said shafts having the form of right circular cylinders, and said lower ends of said shafts being hemispherical in shape so as to prevent injury to the inner ear; and a transverse member affixed to the upper ends of said shafts, and extending between them perpendicular to their axes, of a length corresponding to the distance between the ears of the dog upon which the device will be used, so that said columnar shafts, when inserted into the dog's ear canal, are spaced symmetrically apart.

* * * * *